United States Patent
Maguire

(10) Patent No.: US 6,827,696 B1
(45) Date of Patent: Dec. 7, 2004

(54) ANKLE-FOOT ORTHOSIS

(76) Inventor: Mark T. Maguire, 4869 Robin Hill Dr., Omaha, NE (US) 68106

( * ) Notice: Subject to any disclaimer, the term of this patent is extended or adjusted under 35 U.S.C. 154(b) by 182 days.

(21) Appl. No.: 10/159,430

(22) Filed: May 30, 2002

(51) Int. Cl.$^7$ .................................................. A61F 5/00
(52) U.S. Cl. .............................. 602/27; 602/5; 602/16; 602/23; 602/65
(58) Field of Search .............................. 602/12, 16, 23, 602/27, 28, 29, 62, 65; D24/192; 623/47; 128/882, 869

(56) References Cited

U.S. PATENT DOCUMENTS

| | | | |
|---|---|---|---|
| RE30,501 E | | 2/1981 | Almeida |
| 4,263,902 A | | 4/1981 | Dieterich |
| D272,281 S | | 1/1984 | Alush |
| 4,641,639 A | * | 2/1987 | Padilla .......................... 602/23 |
| 4,974,583 A | * | 12/1990 | Freitas .......................... 602/24 |
| 5,020,523 A | * | 6/1991 | Bodine .......................... 602/27 |
| 5,183,036 A | * | 2/1993 | Spademan .................... 602/10 |
| 5,250,021 A | * | 10/1993 | Chang .......................... 602/27 |
| 5,441,015 A | | 8/1995 | Farley |
| 5,499,461 A | * | 3/1996 | Danezin et al. ............. 36/117.2 |
| 5,697,893 A | | 12/1997 | Rhenter |
| 5,725,489 A | | 3/1998 | Bar-Or et al. |
| 5,865,778 A | * | 2/1999 | Johnson ........................ 602/27 |
| 5,937,546 A | * | 8/1999 | Messmer ....................... 36/89 |
| 5,944,678 A | * | 8/1999 | Hubbard ...................... 602/27 |
| 6,178,555 B1 | * | 1/2001 | Williams .......................... 2/22 |
| D448,484 S | | 9/2001 | Bradshaw |
| 6,299,587 B1 | | 10/2001 | Birmingham |
| 6,319,218 B1 | | 11/2001 | Birmingham |
| 6,350,246 B1 | | 2/2002 | DeToro et al. |
| 6,357,054 B1 | * | 3/2002 | Bainbridge et al. ............. 2/455 |
| 6,409,692 B1 | * | 6/2002 | Covey ........................... 602/5 |
| 2003/0125653 A1 | * | 7/2003 | Meyer ........................ 602/27 |

* cited by examiner

Primary Examiner—Henry Bennett
Assistant Examiner—Amanda Flynn
(74) Attorney, Agent, or Firm—Thomte, Mazour & Niebergall; Dennis L. Thomte

(57) ABSTRACT

An ankle-foot orthosis comprising a generally L-shaped member including a lower leg support having a U-shaped cross section, a U-shaped heel support portion and a foot support portion. The lower leg support portion partially embraces the rearward side of the lower leg of the patient while the heel support portion embraces a portion of the patient's heel. A total contact ankle support having an upper end, a lower end and opposite sides is pivotally secured, at the lower ends thereof, to the opposite sides of the heel support portion with the ankle support being movable between open and closed positions. The ankle support may be moved to its open position to enable the patient to easily don the orthosis. A first connector, retainer or strap extends between the opposite sides of the lower leg portion, above the ankle support, to maintain the patient's leg therein. A second connector, retainer or strap extends between the opposite sides of the lower leg support portion around the ankle support to maintain the ankle support in its closed position.

11 Claims, 3 Drawing Sheets

ANKLE-FOOT ORTHOSIS

BACKGROUND OF THE INVENTION

1. Field of the Invention

This invention relates to an orthosis device, and more particularly to an ankle-foot orthosis.

2. Description of the Related Art

An ankle-foot orthosis (AFO) is used to control the alignment and motions of the joints of the ankle and foot of a patient. Some diagnoses treated with an ankle-foot orthosis are heel cord contracture, stroke, head injury, tone, hypertoxicity, spasticity, etc. Generally speaking, a conventional AFO comprises a metal or plastic upper support for supporting the lower portion of a patient's leg and a heel and foot supporting portion extending forwardly from the lower end of the lower leg supporting portion. Normally, the AFO is strapped onto the patient's lower leg, ankle and foot. The AFOs of the prior art generally function fine for most people, but do not function well enough for those people who require additional total contact ankle support.

SUMMARY OF THE INVENTION

An ankle-foot orthosis is described which includes a generally L-shaped member including a lower leg support portion which has a U-shaped cross section, a U-shaped heel support portion, and a foot support portion. The lower leg support portion partially embraces the rearward side of the lower leg of the patient. The heel support portion embraces the patient's heel. An ankle support having an upper end, a lower end and opposite sides is also provided. The opposite sides of the ankle support are pivotally secured, at the lower ends thereof, to the opposite sides of the heel support portion. The ankle support is pivotally movable between open and closed positions. A first strap extends between the opposite sides of the lower leg support portion to maintain the patient's leg therein. A second strap extends between the opposite sides of the lower leg support portion around the ankle support to maintain the ankle support in its closed position. The total contact ankle support provides proper support for the patient's ankle.

A principal object of the invention is to provide an improved ankle-foot orthosis.

Still another object of the invention is to provide an improved ankle-foot orthosis which includes a generally L-shaped member for total contact support of the lower leg of the wearer, a U-shaped heel support portion, and a foot support portion and further having an ankle support which is pivotally connected to the L-shaped member for supporting the ankle of the wearer.

Still another object of the invention is to provide an ankle-foot orthosis including a pivotal ankle support which is movable between open and closed positions.

Still another object of the invention is to provide an ankle-foot orthosis which includes a total contact ankle support which may be pivoted to an "open" position for ease of donning and for structural stability.

These and other objects will be apparent to those skilled in the art.

DESCRIPTION OF THE PREFERRED EMBODIMENT

Figure 1:
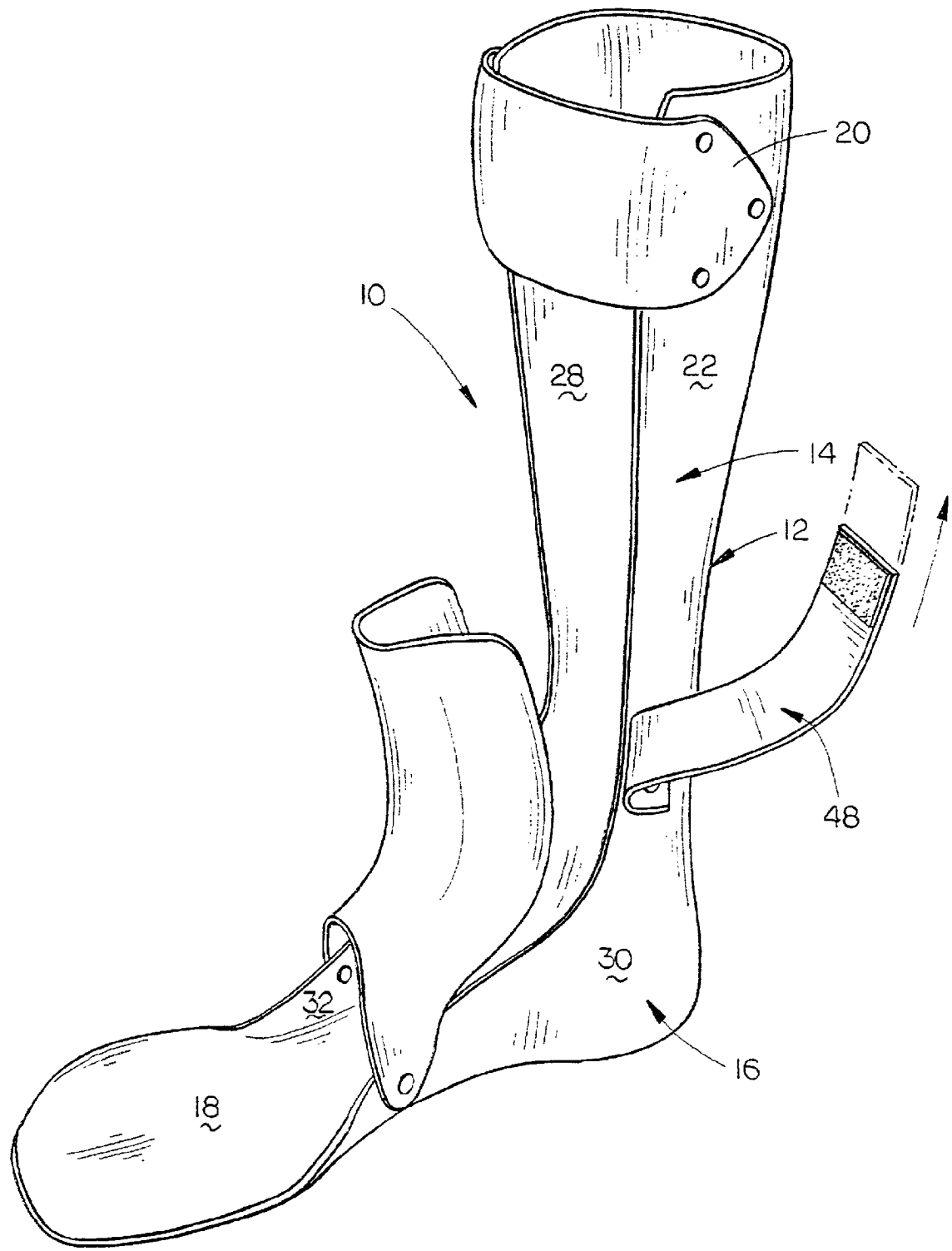
FIG. 1 is a perspective view of the orthosis of this invention.

The ankle-foot orthosis of this invention is referred to generally by the reference numeral 10 which is comprised of a generally L-shaped support 12 including a leg support portion 14, heel support portion 16, and foot support portion 18. Leg support portion 14 is generally U-shaped in cross section and is designed to partially embrace the lower leg of the person wearing the orthosis. Foot support portion 18 is generally flat but may have significant contours in the arch for support and control of the foot.

Figure 3:
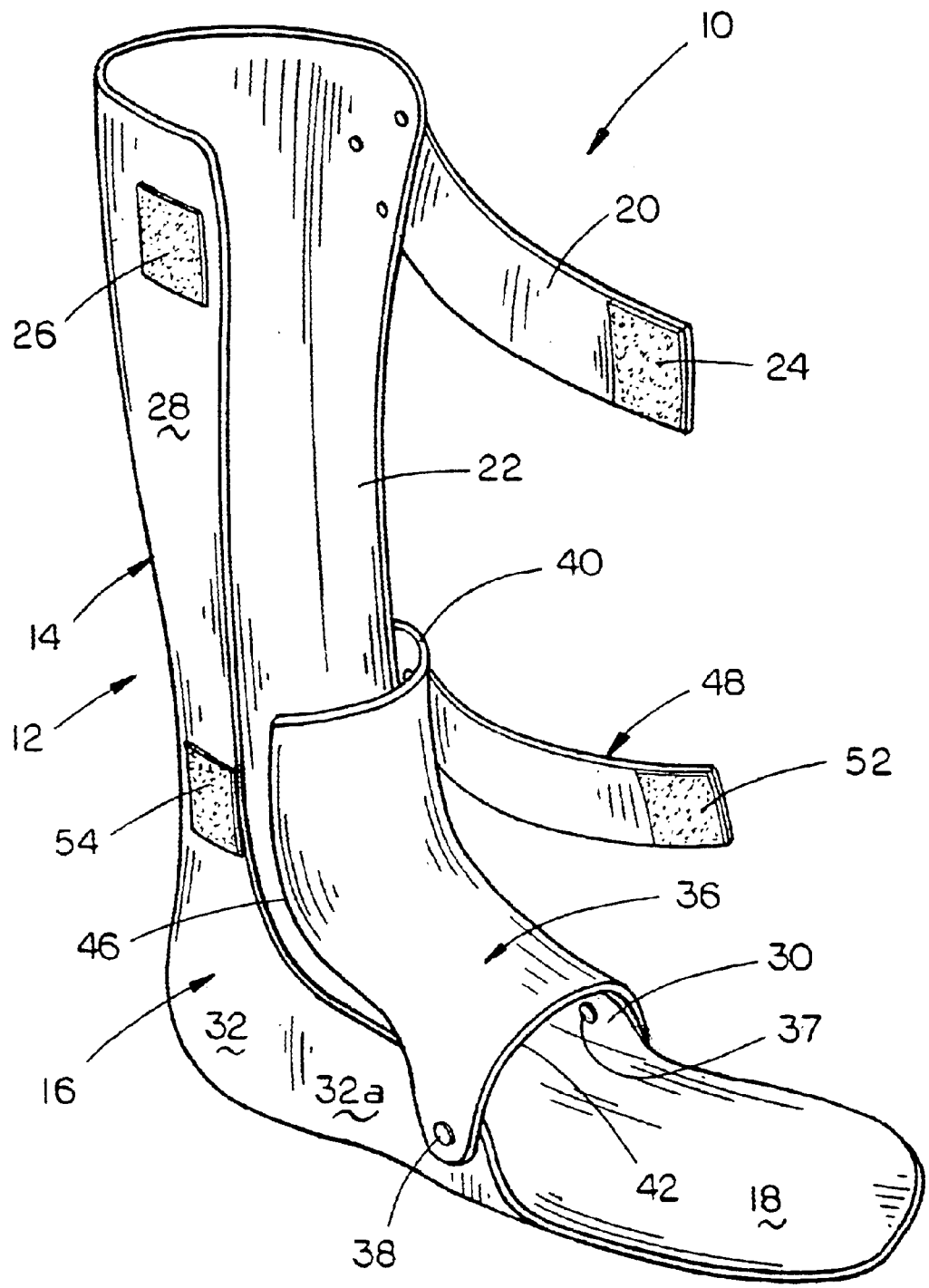
FIG. 3 is a perspective view of the orthosis of this invention prior to the patient inserting his/her lower leg, ankle and foot thereinto.

Strap or retainer 20 is secured to side 22 of leg support portion 14 and has a Velcro® strip 24 secured thereto, as seen in Figure, which is adapted to be secured to the Velcro® strip 26 secured to side 28 of leg support portion 14, as also seen in FIG. 3.

Heel support portion 16 is also generally U-shaped in cross section and is designed to receive the heel of the person wearing the orthosis 10. For purposes of description, heel support portion 16 will be described as including sides 30, 32 and back 34. As seen, the sides 30 and 32 extend forwardly from back 34 so as to be positioned on opposite sides of the person's heel. The sides 30 and 32 extend forwardly sufficiently so as to be positioned on opposite sides of the person's foot as well. For purposes of description, the forward ends of sides 30 and 32 will be designated as forward end portions 30a and 32a, respectively.

The numeral 36 refers to a total contact ankle support which is pivoted to the forward ends 30a and 32a of sides 30 and 32 at 37 and 38, respectively. Ankle support 36 is generally U-shaped in cross section and is generally L-shaped when viewed from the side thereof. Ankle support 36 will be described as including an upper end 40, lower end 42, and opposite side edges 44 and 46. Ankle support 36 is selectively movable between the "open" position of FIG. 1 to the "closed" position of FIG. 2. When the ankle support 36 is in the "open" position of FIG. 1, the patient is easily able to insert his/her foot into the AFO. When in the closed position, the ankle support 36 provides total contact support for the ankle and lends structural stability to the AFO.

Figure 2:
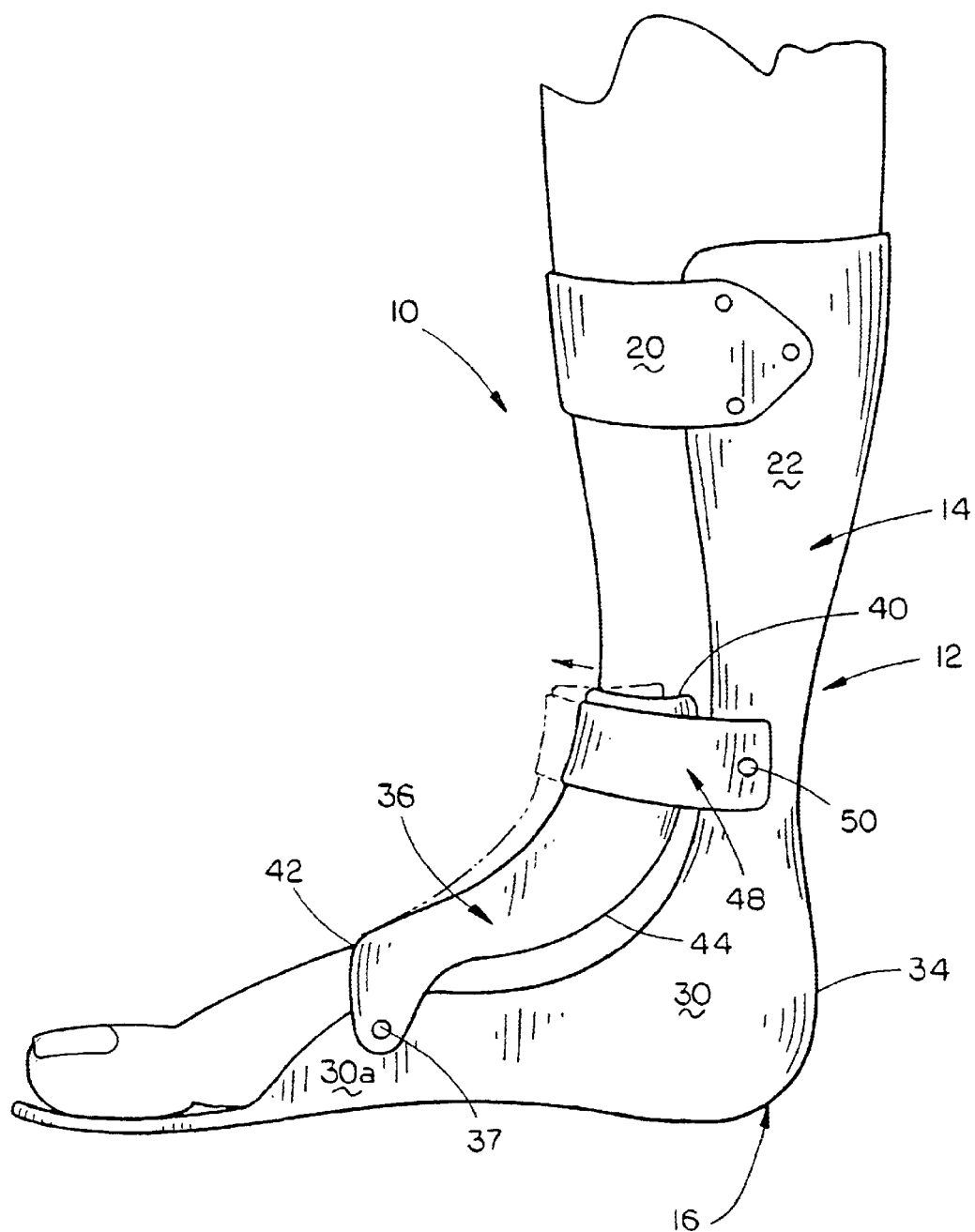
FIG. 2 is a side view of the orthosis of this invention supporting a person's lower leg, ankle and foot.

Strap or retainer 48 has one end thereof secured to side 22 of leg support 14 at 50. The free end of strap 48 has a Velcro® strip 52 secured thereto (FIG. 3) which is adapted to be secured to Velcro® strip 54 secured to side 28 of leg support 14, as seen in FIG. 3. Strap 48 is designed to maintain ankle support 36 in its closed position, as seen in FIG. 2. Although the straps 20 and 48 and the Velcro® strips thereon are the preferred means for maintaining the ankle support 36 in its closed position, other types of connectors or retainers could be used such as those used on ski boots or the like.

The interior surfaces of the orthosis 10 may have padding thereon for reasons of comfort to the wearer. The orthosis is used as follows. Straps 20 and 48 are disconnected from the strips 26 and 54, respectively. Ankle support 36 is pivotally moved to position of FIG. 1. The person then inserts his/her foot, ankle and lower leg into the orthosis 10 with the "open" position of the ankle support enabling the AFO to be easily donned. Ankle support 36 is then pivotally moved rearwardly with respect to leg support 14 so that the inner surface thereof is positioned against the person's foot, ankle and lower leg. The strap 48 is then secured to strip 54 to maintain the ankle support 36 in the closed position of FIG. 2. Strap 20 is then secured to strip 26 to maintain the person's lower leg in the orthosis 10.

Although it is preferred that the AFO be comprised of a plastic material, the AFO could be constructed of a lamination material such as fiberglass, etc.

The orthosis of this invention provides the necessary support for the device to make the orthosis more usable and comfortable to wear, primarily through the use of the ankle support 36 which supports the foot and ankle of the wearer but which permits the AFO to be easily donned.

It is preferred that the AFO be inflexible. However, in some special situations, it may be desirable to provide an ankle joint for some flexibility.

Thus it can be seen that the invention accomplishes at least all of its stated objectives.

I claim:

1. An ankle-foot orthosis, comprising:

generally L-shaped member including a leg support portion having a generally U-shaped cross section, a U-shaped heel support, and a foot support portion;

said leg support portion having a back and opposite sides;

said heel support portion having a back and upwardly extending opposite sidewalls;

an ankle support having an upper end, a lower end and downwardly extending opposite sidewalls;

said downwardly extending opposite sidewalls of said ankle support being pivotally secured, at the lower ends thereof, to said upwardly extending opposite sidewalls of said heel support portion;

said ankle support being movable between open and closed positions;

a first retainer extending between said opposite sides of said leg support portion to maintain the patient's leg therein;

and a second retainer operatively connected to said ankle support to maintain said ankle support in its said closed position.

2. The orthosis of claim 1 wherein said second retainer comprises an elongated strap which extends between said opposite sides of said leg support portion around said ankle support.

3. The orthosis of claim 1 wherein said L-shaped member is comprised of a plastic material.

4. The orthosis of claim 1 wherein said L-shaped member is comprised of a fiberglass material.

5. The orthosis of claim 1 wherein said ankle support is comprised of a plastic material.

6. The orthosis of claim 1 wherein said ankle support is comprised of a fiberglass material.

7. The orthosis of claim 2 wherein said ankle support is comprised of a plastic material.

8. The orthosis of claim 1 wherein said ankle support has a generally U-shaped cross section.

9. The orthosis of claim 8 wherein said ankle support is generally L-shaped when viewed from the side thereof.

10. The orthosis of claim 1 wherein said heel support is generally U-shaped in cross section.

11. The orthosis of claim 1 wherein said foot portion is generally flat.

* * * * *